United States Patent
Sfeir et al.

(10) Patent No.: US 10,760,081 B2
(45) Date of Patent: Sep. 1, 2020

(54) COMPOSITIONS AND METHODS FOR ENHANCING CRISPR ACTIVITY BY POLQ INHIBITION

(71) Applicant: New York University, New York, NY (US)

(72) Inventors: Agnel Sfeir, New York, NY (US); Pedro Mateos-Gomez, New York, NY (US)

(73) Assignee: New York University, New York, NY (US)

( * ) Notice: Subject to any disclaimer, the term of this patent is extended or adjusted under 35 U.S.C. 154(b) by 225 days.

(21) Appl. No.: 15/766,256

(22) PCT Filed: Oct. 7, 2016

(86) PCT No.: PCT/US2016/055967
§ 371 (c)(1),
(2) Date: Apr. 5, 2018

(87) PCT Pub. No.: WO2017/062754
PCT Pub. Date: Apr. 13, 2017

(65) Prior Publication Data
US 2018/0305697 A1 Oct. 25, 2018

Related U.S. Application Data

(60) Provisional application No. 62/238,192, filed on Oct. 7, 2015.

(51) Int. Cl.
| | |
|---|---|
| *C12N 15/00* | (2006.01) |
| *C12N 15/113* | (2010.01) |
| *C12N 9/22* | (2006.01) |
| *C12N 15/90* | (2006.01) |
| *C12N 15/10* | (2006.01) |
| *A61K 48/00* | (2006.01) |
| *A61K 31/7088* | (2006.01) |
| *A61K 38/45* | (2006.01) |
| *C07K 14/47* | (2006.01) |

(52) U.S. Cl.
CPC ...... *C12N 15/1137* (2013.01); *A61K 31/7088* (2013.01); *A61K 38/45* (2013.01); *A61K 48/00* (2013.01); *C07K 14/4703* (2013.01); *C12N 9/22* (2013.01); *C12N 15/102* (2013.01); *C12N 15/907* (2013.01); *C12Y 207/07007* (2013.01); *C12N 2310/20* (2017.05); *C12N 2510/00* (2013.01); *C12N 2800/80* (2013.01)

(58) Field of Classification Search
None
See application file for complete search history.

(56) References Cited

U.S. PATENT DOCUMENTS

| | | |
|---|---|---|
| 2012/0021935 A1 | 1/2012 | Cazaux et al. |
| 2015/0020223 A1 | 1/2015 | Zhang et al. |
| 2015/0232881 A1 * | 8/2015 | Glucksmann ......... C12N 15/63 514/44 R |

OTHER PUBLICATIONS

Mateos-Gomez, P.A., et al., Mammalian Polymerase Theta Promotes Alternative—NHEJ and Suppresses Recomination, Nature, Feb. 12, 2015, vol. 518, No. 7538, pp. 254-257.

Ceccaldi, R., et al., Homologous recombination-deficient tumors are hyper-dependent on POLQ-mediated repair, Nature, Feb. 12, 2015, vol. 518, No. 7538, pp. 258-262.

Mali, P., et al., RNA-Guided Human Genome Engineering via Cas9, Science, Jan. 3, 2013, vol. 339, pp. 823-826 and Supplementary Materials pp. 1-36.

Van Schendel et al., Polymerase Y is a key driver of genome evolution and of CRISPR/Cas9-mediated mutagenesis, Nature Communications, 6:7394 Jun. 16, 2015.

* cited by examiner

*Primary Examiner* — Catherine S Hibbert
(74) *Attorney, Agent, or Firm* — Hodgson Russ LLP

(57) ABSTRACT

Provided are approaches to improving CRISPR-based DNA editing by performing the editing in cells in which pol Θ ("POLQ") enzyme and/or its function is reduced. Approaches are provided that are applicable to Cas9 nuclease and Cas9 nickase CRISPR editing. Also provided are kits that can contain a polynucleotide encoding a Cas9 and an agent for use in inhibiting POLQ, and/or or an expression vector configured for expressing a mutation template for use in CRISPR chromosome editing and an agent for use in inhibiting POLQ.

9 Claims, 8 Drawing Sheets
Specification includes a Sequence Listing.

Figure 2

Guide RNAs for Sox2 (DNA sequence is SEQ ID NO:1; amino acid sequence is SEQ ID NO:2):

Figure 2 (continued)

Template plasmid for Sox2 (DNA sequence is SEQ ID NO:3; amino acid sequence is SEQ ID NO:4):

Figure 3

Primers for Sox2 genotyping (SEQ ID NO:5):

Guide RNAs for Hsp90ab1 (SEQ ID NO:6):

Figure 4 (continued)

Template for Hsp90ab1 (SEQ ID NO:7):

Figure 4 (continued)

Template for Hsp90ab1 (SEQ ID NO:7):

SEQUENCE LISTING

```
<160> NUMBER OF SEQ ID NOS: 21

<210> SEQ ID NO 1
<211> LENGTH: 330
<212> TYPE: DNA
<213> ORGANISM: artificial sequence
<220> FEATURE:
<223> OTHER INFORMATION: guide RNA

<400> SEQUENCE: 1
gccaggccgg ggacctccgg gacatgatca gcatgtacct ccccggcgcc gaggtgccgg      60
agcccgctgc gcccagtaga ctgcacatgg cccagcacta ccagagcggc ccggtgcccg     120
```

```
gcacggccat taacggcaca ctgcccctgt cgcacatgtg agggctggac tgcgaactgg    180
agaaggggag agattttcaa agagatacaa gggaattggg aggggtgcaa aagaggaga    240 gtaggaaaaa tctgataatg ctcaaaagga aaaaaatct ccgcagcgaa acgacagctg    300
cggaaaaaaa ccaccaatcc catccaaatt                                    330
```

<210> SEQ ID NO 2
<211> LENGTH: 136
<212> TYPE: PRT
<213> ORGANISM: mouse
<400> SEQUENCE: 2

```
Glu Ala Ser Ser Ser Pro Pro Val Val Thr Ser Ser His Ser Arg
1               5                   10                  15

Ala Pro Cys Gln Ala Gly Asp Leu Arg Asp Met Ile Ser Met Tyr Leu
            20                  25                  30

Pro Gly Ala Glu Val Pro Glu Pro Ala Ala Pro Ser Arg Leu His Met
        35                  40                  45

Ala Gln His Tyr Gln Ser Gly Pro Val Pro Gly Thr Ala Ile Asn Gly
    50                  55                  60

Thr Leu Pro Leu Ser His Met Gly Leu Asp Cys Glu Leu Glu Lys Gly
65                  70                  75                  80

Arg Asp Phe Gln Arg Asp Thr Arg Glu Leu Gly Gly Val Gln Lys Glu
                85                  90                  95

Glu Ser Arg Lys Asn Leu Ile Met Leu Lys Arg Lys Lys Asn Leu Arg
            100                 105                 110

Ser Glu Thr Thr Ala Ala Glu Lys Asn His Gln Ser His Pro Asn Arg
        115                 120                 125

Lys Asn Arg Asp Ala Asp Lys Thr
    130                 135
```

<210> SEQ ID NO 3
<211> LENGTH: 1299
<212> TYPE: DNA
<213> ORGANISM: artificial sequence
<220> FEATURE:
<223> OTHER INFORMATION: recombinant plasmid sequence segment
<400> SEQUENCE: 3

```
ctccatgacc agctcgcaga cctacatgaa cggctcgccc acctacagca tgtcctactc    60
gcagcagggc accccggta tggcgctggg ctccatgggc tctgtggtca agtccgaggc    120
cagctccagc ccccccgtgg ttacctcttc ctcccactcc agggcgccct gccaggccgg    180
ggacctccgg gacatgatca gcatgtacct ccccggcgcc gaggtgccgg agcccgctgc    240
gcccagtaga ctgcacatgg cccagcacta ccagagcggc ccggtgcccg gcacggccat    300
taacggcaca ctgcccctgt cgcacatggg atcgggagcc acaaacttct ctctgctaaa    360
gcaagcaggt gatgttgaag aaaaccccgg gcctatggcc cagtccaagc acggcctgac    420
caaggagatg accatgaagt accgcatgga gggctgcgtg gacggccaca gttcgtgat    480 caccggcgag ggcatcggct acccttcaa gggcaagcag gccatcaacc tgtgcgtggt    540
ggagggcggc cccttgccct cgccgaggca catcttgtcc gccgccttca tgtacggcaa    600
ccgcgtgttc accgagtacc ccaggacat cgtcgactac ttcaagaact cctgccccgc    660
cggctacacc tggaccgct ccttcctgtt cgaggacggc gccgtgtgca tctgcaacgc    720
cgacatcacc gtgagcgtgg aggagaactg catgtaccac gagtccaagt ctacggcgt    780
```

```
gaacttcccc gccgacggcc ccgtgatgaa aagatgacc gacaactggg agccctcctg    840
cgagaagatc atccccgtgc ccaagcaggg catcttgaag ggcgacgtga gcatgtacct    900
gctgctgaag gacggtggcc gcttgcgctg ccagttcgac accgtgtaca aggccaagtc    960
cgtgccccgc aagatgcccg actggcactt catccagcac aagctgaccc gcgaggaccg   1020
cagcgacgcc aagaaccaga gtggcacct gaccgagcac gccatcgcct ccggctccgc   1080
cttgccctaa gggctggact gcgaactgga aaggggaga gattttcaaa gagatacaag   1140
ggaattggga ggggtgcaaa aagaggagag taggaaaaat ctgataatgc tcaaaaggaa   1200
aaaaaatctc cgcagcgaaa cgacagctgc ggaaaaaaac caccaatccc atccaaatta   1260
acgcaaaaac cgtgatgccg actagaaaac ttttatgag                          1299
```

<210> SEQ ID NO 4
<211> LENGTH: 429
<212> TYPE: PRT
<213> ORGANISM: artificial sequence
<220> FEATURE:
<223> OTHER INFORMATION: protein encoded by recombinant plasmid

<400> SEQUENCE: 4

```
Ser Met Thr Ser Ser Gln Thr Tyr Met Asn Gly Ser Pro Thr Tyr Ser
1               5                   10                  15

Met Ser Tyr Ser Gln Gln Gly Thr Pro Gly Met Ala Leu Gly Ser Met
            20                  25                  30

Gly Ser Val Val Lys Ser Glu Ala Ser Ser Pro Val Val Thr
        35                  40                  45

Ser Ser His Ser Arg Ala Pro Cys Gln Ala Gly Asp Leu Arg Asp
    50                  55                  60

Met Ile Ser Met Tyr Leu Pro Gly Ala Glu Val Pro Glu Pro Ala Ala
65                  70                  75                  80

Pro Ser Arg Leu His Met Ala Gln His Tyr Gln Ser Gly Pro Val Pro
                85                  90                  95

Gly Thr Ala Ile Asn Gly Thr Leu Pro Leu Ser His Met Gly Ser Gly
            100                 105                 110

Ala Thr Asn Phe Ser Leu Leu Lys Gln Ala Gly Asp Val Glu Glu Asn
        115                 120                 125

Pro Gly Pro Met Ala Gln Ser Lys His Gly Leu Thr Lys Glu Met Thr
    130                 135                 140

Met Lys Tyr Arg Met Glu Gly Cys Val Asp Gly His Lys Phe Val Ile
145                 150                 155                 160

Thr Gly Glu Gly Ile Gly Tyr Pro Phe Lys Gly Lys Gln Ala Ile Asn
                165                 170                 175

Leu Cys Val Val Glu Gly Gly Pro Leu Pro Phe Ala Glu Asp Ile Leu
            180                 185                 190

Ser Ala Ala Phe Met Tyr Gly Asn Arg Val Phe Thr Glu Tyr Pro Gln
        195                 200                 205

Asp Ile Val Asp Tyr Phe Lys Asn Ser Cys Pro Ala Gly Tyr Thr Trp
    210                 215                 220

Asp Arg Ser Phe Leu Phe Glu Asp Gly Ala Val Cys Ile Cys Asn Ala
225                 230                 235                 240

Asp Ile Thr Val Ser Val Glu Glu Asn Cys Met Tyr His Glu Ser Lys
                245                 250                 255

Phe Tyr Gly Val Asn Phe Pro Ala Asp Gly Pro Val Met Lys Lys Met
            260                 265                 270
```

```
Thr Asp Asn Trp Glu Pro Ser Cys Glu Lys Ile Ile Pro Val Pro Lys
            275                 280                 285

Gln Gly Ile Leu Lys Gly Asp Val Ser Met Tyr Leu Leu Leu Lys Asp
        290                 295                 300

Gly Gly Arg Leu Arg Cys Gln Phe Asp Thr Val Tyr Lys Ala Lys Ser
305                 310                 315                 320

Val Pro Arg Lys Met Pro Asp Trp His Phe Ile Gln His Lys Leu Thr
                325                 330                 335

Arg Glu Asp Arg Ser Asp Ala Lys Asn Gln Lys Trp His Leu Thr Glu
            340                 345                 350

His Ala Ile Ala Ser Gly Ser Ala Leu Pro Gly Leu Asp Cys Glu Leu
        355                 360                 365

Glu Lys Gly Arg Asp Phe Gln Arg Asp Thr Arg Glu Leu Gly Gly Val
    370                 375                 380

Gln Lys Glu Glu Ser Arg Lys Asn Leu Ile Met Leu Lys Arg Lys Lys
385                 390                 395                 400

Asn Leu Arg Ser Glu Thr Thr Ala Ala Glu Lys Asn His Gln Ser His
                405                 410                 415

Pro Asn Arg Lys Asn Arg Asp Ala Asp Lys Thr Phe Met
                420                 425

<210> SEQ ID NO 5
<211> LENGTH: 2090
<212> TYPE: DNA
<213> ORGANISM: artificial sequence
<220> FEATURE:
<223> OTHER INFORMATION: Sox2 related sequences

<400> SEQUENCE: 5
cgccggcggg ccgcgcccgc ccagcgcccg catgtataac atgatggaga cggagctgaa      60
gccgccgggc ccgcagcaag cttcgggggg cggcggcgga ggaggcaacg ccacggcggc     120
ggcgaccggg ggcaaccaga agaacagccc ggaccgcgtc aagaggccca tgaacgcctt     180
catggtatgg tcccgggggc agcggcgtaa gatggcccag gagaacccca gatgcacaa     240
ctcggagatc agcaagcgcc tgggcgcgga gtggaaactt ttgtccgaga ccgagaagcg     300
gccgttcatc gacgaggcca gcggctgcg cgctctgcac atgaaggagc accggatta      360
taaataccgg ccgcggcgga aaaccaagac gctcatgaag aaggataagt acacgcttcc     420
cggaggcttg ctggccccg gcgggaacag catggcgagc ggggttgggg tgggcgccgg     480
cctgggtgcg ggcgtgaacc agcgcatgga cagctacgcg cacatgaacg gctggagcaa     540
cggcagctac agcatgatgc aggagcagct gggctacccg cagcacccgg gcctcaacgc     600
tcacggcgcg gcacagatgc aaccgatgca ccgctacgac gtcagcgccc tgcagtacaa     660
ctccatgacc agctcgcaga cctacatgaa cggctcgccc acctacagca tgtcctactc     720
gcagcagggc acccccggta tggcgctggg ctccatgggc tctgtggtca agtccgaggc     780
cagctccagc ccccccgtgg ttacctcttc ctcccactcc agggcgccct gccaggccgg     840
ggacctccgg gacatgatca gcatgtacct ccccggcgcc gaggtgccgg agcccgctgc     900
gcccagtaga ctgcacatgg cccagcacta ccagagcggc ccgatgccg cacggccat      960
taacggcaca ctgcccctgt cgcacatggg atcgggagcc acaaacttct ctctgctaaa    1020
gcaagcaggt gatgttgaag aaaaccccgg ccctatggcc cagtccaagc acggcctgac    1080
caaggagatg accatgaagt accgcatgga gggctgcgtg acggccaca agttcgtgat    1140
caccggcgag ggcatcggct accccttcaa gggcaagcag gccatcaacc tgtgcgtggt    1200
```

```
ggagggcggc cccttgccct tcgccgagga catcttgtcc gccgccttca tgtacggcaa    1260
ccgcgtgttc accgagtacc cccaggacat cgtcgactac ttcaagaact cctgccccgc    1320
cggctacacc tgggaccgct ccttcctgtt cgaggacggc gccgtgtgca tctgcaacgc    1380
cgacatcacc gtgagcgtgg aggagaactg catgtaccac gagtccaagt tctacggcgt    1440
gaacttcccc gccgacggcc ccgtgatgaa gaagatgacc gacaactggg agccctcctg    1500
cgagaagatc atccccgtgc ccaagcaggg catcttgaag ggcgacgtga gcatgtacct    1560
gctgctgaag gacggtggcc gcttgcgctg ccagttcgac accgtgtaca aggccaagtc    1620
cgtgccccgc aagatgcccg actggcactt catccagcac aagctgaccc gcgaggaccg    1680
cagcgacgcc aagaaccaga gtggcacct gaccgagcac gccatcgcct ccggctccgc    1740
cttgccctaa gggctggact gcgaactgga aaggggaga gattttcaaa gagatacaag    1800
ggaattggga ggggtgcaaa agaggagag taggaaaaat ctgataatgc tcaaaaggaa    1860
aaaaaatctc cgcagcgaaa cgacagctgc ggaaaaaaac caccaatccc atccaaatta    1920
acgcaaaaac cgtgatgccg actagaaaac ttttatgaga gatcttggga cttcttttg     1980 ggggactatt tttgtacaga gaaaacctga gggcggcggg gagggcgggg aatcggacc    2040 atgtatagat ctggaggaaa aaaactacgc aaaacttttt tttaaagttc                2090
```

<210> SEQ ID NO 6
<211> LENGTH: 300
<212> TYPE: DNA
<213> ORGANISM: artificial sequence
<220> FEATURE:
<223> OTHER INFORMATION: guide RNA sequence

<400> SEQUENCE: 6

```
gagatccccc ctctggaagg cgatgaggat gcctcgcgca tggaagaggt ggattaaagc     60
ctcctggaag aagccctgcc ctctgtatag tatccccgtg gctcccccag cagccctgac    120
ccacctggct ctctgctcat gtctacaaga atcttctatc ctgtcctgtg ccttaaggca    180
ggaagatccc ctcccacaga atagcagggt tgggtgttat gtattgtggt ttttttgttt    240
gttttatttt gttctaaaat taaaagtatg caaaataaag aagatgcagt tttatacagt    300
```

<210> SEQ ID NO 7
<211> LENGTH: 2174
<212> TYPE: DNA
<213> ORGANISM: artificial sequence
<220> FEATURE:
<223> OTHER INFORMATION: recombinant plasmid segment

<400> SEQUENCE: 7

```
caggttatcc ttgaatccct gtactcaagc aaccttcagt ctccagagca tgtaaggggg     60
ttagtcctct gcctgccatc ttagtaaggt tcttcataca tagcagttcc attatggcca    120
aggtacatct tgtcattgtt cttgattgtc cacaggtgac aatctccaat aggcttgtgt    180
cttcaccctg ctgcattgtg acaagcacct atggctggac agccaacatg gaacggatca    240
tgaaggccca ggcactgcga gacaactcta caatgggcta catgatggcc aaaaaacacc    300
tggagatcaa ccctgaccac cccatcgtgg agaccctgcg gcagaggct gaggcagaca    360 aaaacgacaa agctgtcaag gacctggtgg tgctgctgtt tgaaactgct ctgctctcct    420
ctggtttctc acttgaggat ccccaaaccc actccaaccg catctaccgc atgattaaac    480
taggcctggg tgagtctggc ttgtgagctc ctggtagcaa gttgttgtac tagctggacc    540
```

```
tttgggcaga cttagtgctt tgtggcttac ttaaatctgt gtctttctct taggcatcga    600
tgaagatgag gtcactgcag aggagcccag tgctgctgtt cctgatgaga tccccctct    660 ggaaggcgat gaggatgcta gtagaatgga agaggtggat ctcgagggat cgggagccac    720
aaacttctct ctgctaaagc aagcaggtga tgttgaagaa acccccgggc ctatggccca    780
gtccaagcac ggcctgacca aggagatgac catgaagtac cgcatggagg gctgcgtgga    840
cggccacaag ttcgtgatca ccggcgaggg catcggctac cccttcaagg gcaagcaggc    900
catcaacctg tgcgtggtgg agggcggccc cttgcccttc gccgaggaca tcttgtccgc    960
cgccttcatg tacggcaacc gcgtgttcac cgagtacccc caggacatcg tcgactactt   1020
caagaactcc tgccccgccg gctacacctg ggaccgctcc ttcctgttcg aggacggcgc   1080
cgtgtgcatc tgcaacgccg acatcaccgt gagcgtggag gagaactgca tgtaccacga   1140
gtccaagttc tacggcgtga acttccccgc cgacggcccc gtgatgaaga gatgaccga   1200 caactgggag ccctcctgcg agaagatcat ccccgtgccc aagcagggca tcttgaaggg   1260
cgacgtgagc atgtacctgc tgctgaagga cggtggccgc ttgcgctgcc agttcgacac   1320
cgtgtacaag gccaagtccg tgccccgcaa gatgcccgac tggcacttca tccagcacaa   1380
gctgacccgc gaggaccgca gcgacgccaa gaaccagaag tggcacctga ccgagcacgc   1440
catcgcctcc ggctccgcct tgccctaagg atccagcctc ctggaagaag ccctgccctc   1500
tgtatagtat ccccgtggct cccccagcag ccctgaccca cctggctctc tgctcatgtc   1560
tacaagaatc ttctatcctg tcctgtgcct taaggcagga agatcccctc ccacagaata   1620
gcagggttgg gtgttatgta ttgtggtttt tttgtttgtt ttattttgtt ctaaaattaa   1680
aagtatgcaa aataaagaag atgcagtttt atacagtcct gctctccttg taacactcag   1740
ggcttcctga gtggtgttgg aaggtgatga aaggcagtta cttgtccatc aactattaat   1800
gccaaccaaa acacaggtcc aaagtcactg ctgcagttta atcaaataag agcaaaaggt   1860
gacatttcca agtaccaaaa cttgggtagg aacactgggg ccccaactgg gctgggggcc   1920
tttgtccctt ctggcacagc accattctca ctggccccta ggggaactgc atgacctgta   1980
aacaattctc ttcccagctg gtgcctggta gcctcaaggg tgcgtgctat gagcaaagcc   2040
ctggtgctgg tttgcttggc caccagcaag atttcagaga ttgggggagg agctctgggt   2100
cacctctaac caaacaccca cagctgtcat ttccatgaag tgggggctct aaggcaaaa    2160 gaggctgcct ccag                                                      2174

<210> SEQ ID NO 8
<211> LENGTH: 20
<212> TYPE: DNA
<213> ORGANISM: artificial sequence
<220> FEATURE:
<223> OTHER INFORMATION: Guide RNA

<400> SEQUENCE: 8
cccgtatccg gcgagccaac                                                   20

<210> SEQ ID NO 9
<211> LENGTH: 20
<212> TYPE: DNA
<213> ORGANISM: artificial sequence
<220> FEATURE:
<223> OTHER INFORMATION: guide RNA

<400> SEQUENCE: 9
actccagtct ttctagaaga                                                   20
```

```
<210> SEQ ID NO 10
<211> LENGTH: 21
<212> TYPE: DNA
<213> ORGANISM: artificial sequence
<220> FEATURE:
<223> OTHER INFORMATION: DNA of shRNA

<400> SEQUENCE: 10
cggcggagta tgagaactat t                                              21

<210> SEQ ID NO 11
<211> LENGTH: 21
<212> TYPE: DNA
<213> ORGANISM: artificial sequence
<220> FEATURE:
<223> OTHER INFORMATION: DNA of guide RNA

<400> SEQUENCE: 11
ccaggaatca aagacgacaa t                                              21

<210> SEQ ID NO 12
<211> LENGTH: 21
<212> TYPE: DNA
<213> ORGANISM: artificial sequence
<220> FEATURE:
<223> OTHER INFORMATION: DNA of gRNA

<400> SEQUENCE: 12
cctggctgaa tgctgaactt t                                              21

<210> SEQ ID NO 13
<211> LENGTH: 21
<212> TYPE: DNA
<213> ORGANISM: artificial sequence
<220> FEATURE:
<223> OTHER INFORMATION: Guide RNA

<400> SEQUENCE: 13
cgggcctctt tagatataaa t                                              21

<210> SEQ ID NO 14
<211> LENGTH: 20
<212> TYPE: DNA
<213> ORGANISM: artificial sequence
<220> FEATURE:
<223> OTHER INFORMATION: Oligonucleotide

<400> SEQUENCE: 14
cagccctcac atgtgcgaca                                                20

<210> SEQ ID NO 15
<211> LENGTH: 20
<212> TYPE: DNA
<213> ORGANISM: artificial sequence
<220> FEATURE:
<223> OTHER INFORMATION: Oligonucleotide

<400> SEQUENCE: 15
cgatgaggat gcctcgcgca                                                20

<210> SEQ ID NO 16
<211> LENGTH: 20
<212> TYPE: DNA
<213> ORGANISM: artificial sequence
<220> FEATURE:
```

```
<223> OTHER INFORMATION: Oligonucleotide

<400> SEQUENCE: 16
ttaatggccg tgccgggcac                                              20

<210> SEQ ID NO 17
<211> LENGTH: 20
<212> TYPE: DNA
<213> ORGANISM: artificial sequence
<220> FEATURE:
<223> OTHER INFORMATION: Oligonucleotide

<400> SEQUENCE: 17
gtgagggctg gactgcgaac                                              20

<210> SEQ ID NO 18
<211> LENGTH: 20
<212> TYPE: DNA
<213> ORGANISM: artificial sequence
<220> FEATURE:
<223> OTHER INFORMATION: Oligonucleotide

<400> SEQUENCE: 18
cgatgaggat gcctcgcgca                                              20

<210> SEQ ID NO 19
<211> LENGTH: 20
<212> TYPE: DNA
<213> ORGANISM: artificial sequence
<220> FEATURE:
<223> OTHER INFORMATION: Oligonucleotide

<400> SEQUENCE: 19
ggggatacta tacagagggc                                              20

<210> SEQ ID NO 20
<211> LENGTH: 20
<212> TYPE: DNA
<213> ORGANISM: artificial sequence
<220> FEATURE:
<223> OTHER INFORMATION: Oligonucleotide

<400> SEQUENCE: 20
ccctctgtat agtatccccg                                              20

<210> SEQ ID NO 21
<211> LENGTH: 20
<212> TYPE: DNA
<213> ORGANISM: artificial sequence
<220> FEATURE:
<223> OTHER INFORMATION: Oligonucleotide

<400> SEQUENCE: 21
atccacctct tccatgcgcg                                              20
```

COMPOSITIONS AND METHODS FOR ENHANCING CRISPR ACTIVITY BY POLQ INHIBITION

CROSS-REFERENCE TO RELATED APPLICATIONS

This application claims priority to U.S. provisional patent application no. 62/238,192, filed Oct. 7, 2015.

FIELD

The present disclosure relates generally to enhancing the efficiency of clustered regularly interspaced short palindromic repeats (CRISPR)-based editing, and more particularly to enhancing the activity of Cas9 in mammalian cells by inhibiting POLQ, an alternative non-homologous end joining (NHEJ) factor, during Cas9 editing.

BACKGROUND

CRISPR-based editing of DNA, including editing of the genome of mammalian cells, has gained widespread notoriety for its potentially significant power to engineer genomes for a multitude of purposes. However, there remains an ongoing need for compositions and methods to improve CRISPR-based genome editing. The present disclosure meets this need.

SUMMARY

The present disclosure provides approaches to improving CRISPR-based DNA editing. Embodiments include performing Cas9 DNA editing in cells in which pol θ ("POLQ") enzyme and/or its function is reduced and/or eliminated. The disclosure is applicable to Cas9 nuclease and Cas9 nickase CRISPR editing. In certain non-limiting implementations the disclosure comprises increasing homozygous targeting, such as when using Cas9 nickase, and increasing both homozygous and heterozygous targeting, such as when Cas9 nuclease is used.

Methods of the disclosure can be performed using cells that have been engineered to express a Cas9, and one or more CRISPR guide RNAs (gRNA) directed to a target DNA sequence in the cell(s). The cells can be engineered to express the Cas9 and gRNAs, as well as other polynucleotides/proteins using a variety of methods that are known in the art. In certain aspects the disclosure comprises introducing into cells a polynucleotide (a mutation template) for modifying a target DNA sequence via CRISPR editing. In non-limiting examples the cells are engineered to express Cas9 and the gRNA and/or the mutation template from a single expression vector, or by distinct expression vectors.

In non-limiting examples POLQ enzyme and/or its function is reduced and/or eliminated in the cells where CRISPR editing is performed. This can be achieved by introducing into the cells an agent capable of inhibiting expression of POLQ, and/or capable of inhibiting its function. In non-limiting embodiments the agent capable of inhibiting POLQ expression comprises a polynucleotide directed to a polynucleotide in the cell that encodes POLQ (a POLQ targeting polynucleotide). In certain implementations the POLQ targeting polynucleotide is selected from the group consisting of an anti sense oligonucleotide, an siRNA, an shRNA, a polynucleotide encoding an shRNA, or a ribozyme, and combinations thereof. The disclosure includes allowing expression of the Cas9 such that the target DNA sequence is modified, wherein the modified DNA sequence comprises an insertion of at least a segment of the mutation template into the target DNA sequence. Detectable markers can also be inserted.

The disclosure is applicable to any mammalian cells and at any stage of cell development. In embodiments the cells are human cells, or are non-human mammal cells. The disclosure includes mammalian cells made by the methods described herein, their progeny, and non-human mammals comprising them. Also provided are kits for use in methods of the invention. The kits can comprise a polynucleotide encoding a Cas9 and an agent for use in inhibiting POLQ. In embodiments the disclosure provides a kit comprising an expression vector configured for expressing a mutation template for use in CRISPR chromosome editing, and further comprises an agent for use in inhibiting POLQ.

DESCRIPTION OF THE FIGURES

FIG. 2. Representative sequences used to illustrate embodiments of this disclosure. Boxes indicate segments of the sequences as labeled. The sequence includes the region within the sox2 gene that was subject to cleavage by Cas9-nuclease and by Cas9 nickase (D10A). The lower part shows the template used for the genome editing. In FIG. 2 the Guide RNA for Sox2 is SEQ ID NO:1 (provided as a cDNA sequence). The Sox2 amino acid sequence is SEQ ID NO:2. The DNA sequence of the Template plasmid for Sox2 is SEQ ID NO:3; the amino acid sequence for the Template plasmid for Sox2 is SEQ ID NO:4. Dots signify a stop codon and are present in 3' untranslated sequences.

Figure 3:
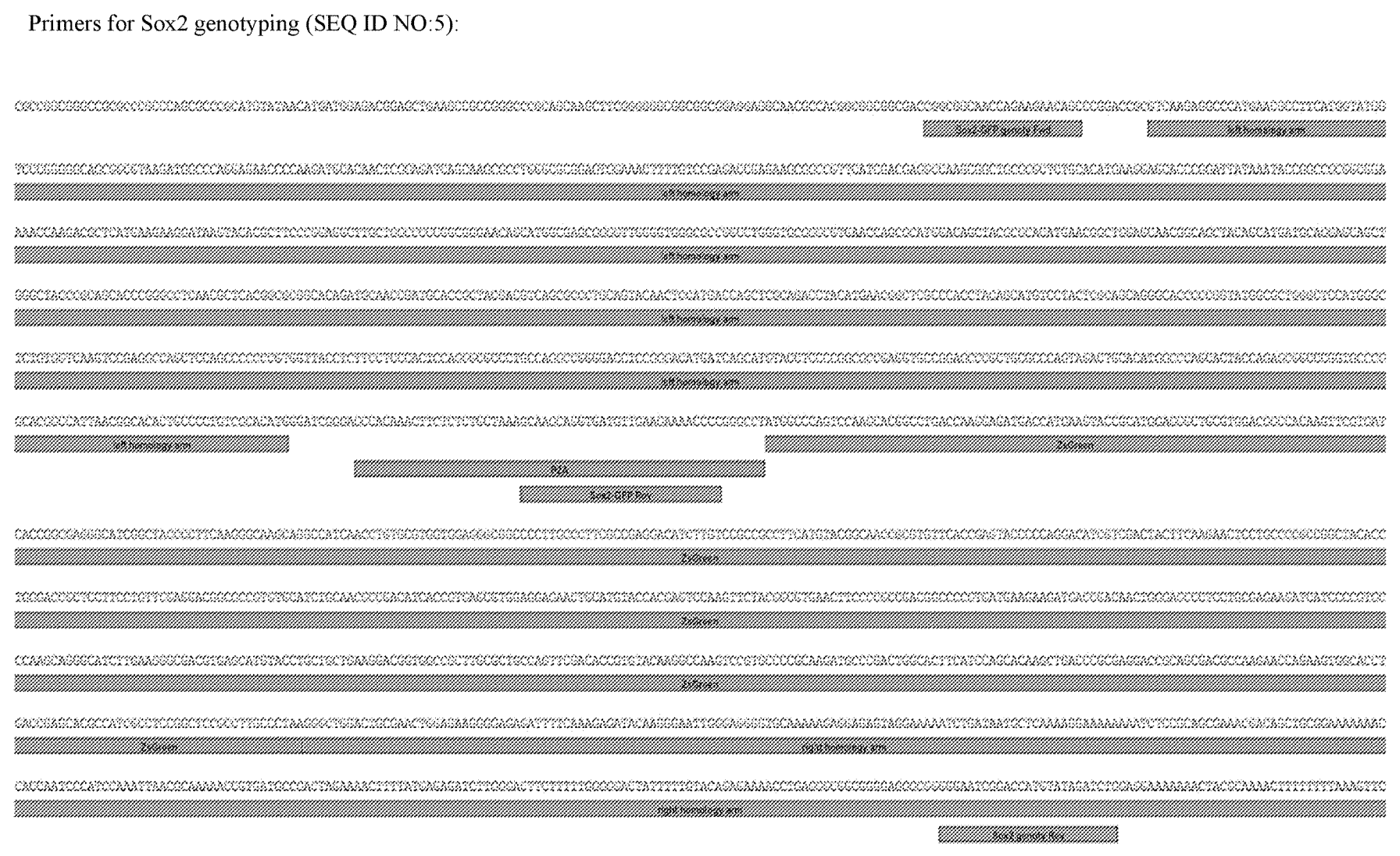

FIG. 3. Representative sequences used to illustrate embodiments of this disclosure; the DNA sequence is SEQ ID NO:5. Boxes indicate segments of the sequences as labeled and show primer sequences that were used to perform genotyping PCR and confirm whether edited Sox2 cells were homozygous or heterozygous.

DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure includes all DNA sequences described herein, their complementary sequences, and the RNA equivalents of the DNA sequences, wherein each T is replaced by a U.

Figure 1B:
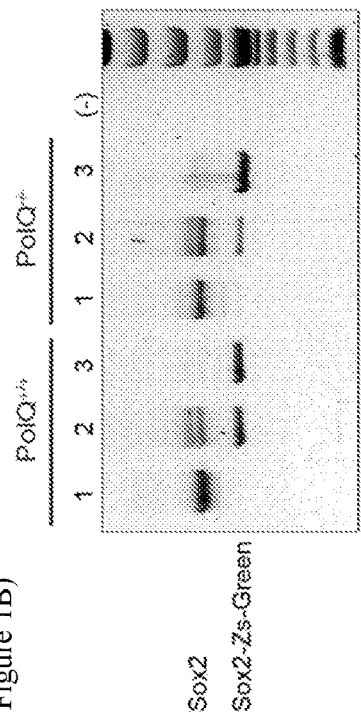
FIG. 1A) Flow cytometry analysis to quantify ZsGreen expression in mouse CCE embryonic stem cells (mESc) (CCE a mES cell line derived from 129/Sv mouse strain; Robertson E, Bradley A, Kuehn M, Evans M, Nature. 1986 Oct. 2-8; 323(6087):445-8. Keller G, Kennedy M, Papayannopoulou T, Wiles M V, Mol Cell Biol. 1993 January; 13(1):473-86. Numbers represent the percentage of cells in each quadrant. Three independent population of CCE mES cells, with distinct ZsGreen intensity were isolated (highlighted in 1, 2 and 3 circles). 1B) Genotyping PCR for Sox2 on DNA extracted from the three highlighted groups of cells (1A) in POLQ proficient (POLQ+/+, WT) and PolQ deficient (PolQ−/−, Null) CCE mES cells. Group 1 depicts non-targeted cells, Group 2 represents cells carrying heterozygous Sox2 cells and in group 3 both alleles of Sox 2 were targeted. 1C) Left, graph depicting results of FACS analysis for ZsGreen positive CCE mES cells (POLQ+/+ and PolQ−/−) treated with the indicated Cas9 nuclease plasmid (also encoding for a gRNA targeting the Sox2 gene) and a donor plasmid with the sequence to be inserted at the end of the gene. DNA-PK inhibitor was used to block repair by classical NHEJ (Non-Homologous End-Joining). Right, cells treated with Cas9-nickase containing plasmid that also encodes for two Sox2 gRNAs. Three independent experiments, each performed in duplicate. The control gRNAs were designed to target two independent loci in the cells (H3F3B and Rosa26, 5'-CCCGTATCCGGCGAGCCAAC-3' (SEQ ID NO:8) and 5'-ACTCCAGTCTTTCTAGAAGA-3' (SEQ ID NO:9), respectively) to which, the donor plasmid has no homology. 1D) Left, depicts results of FACS analysis for ZsGreen positive mES cells (POLQ WT and null, derived from B6.Cg-Polq$^{tm1Jcs}$/J mouse) treated with the indicated Cas9 nuclease and the donor plasmid. The Cas9 plasmid also encodes the gRNA that targets Hsp90ab1. Right, cells treated with a Cas9-nickase containing plasmid that encodes for two Hsp90ab1 gRNAs. This experiment was performed with two different Cas9-nickase plasmids, one encoding two gRNAs that generates 3' overhangs after cleavage and other that generates 5' overhangs). Three independent experiments, each performed in duplicate. 1E) Depicts results of FACS analysis for ZsGreen positive MEFs cells (POLQ WT and null, derived from B6.Cg-Polq$^{tm1Jcs}$/J mouse) treated with the indicated Cas9 as in FIG. 1D. Three independent experiments, each performed in duplicate.
Figure 1A:
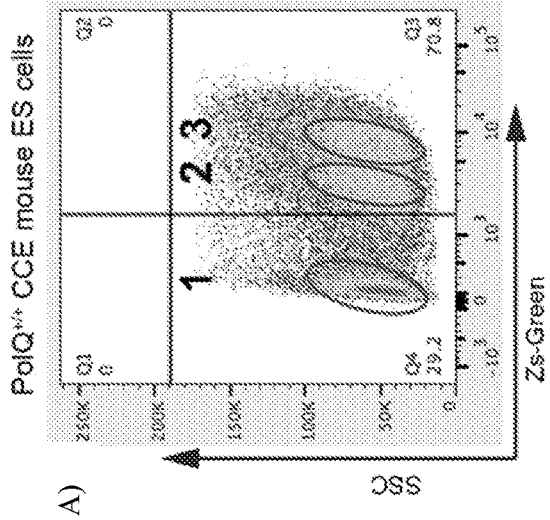
Figure 1C:
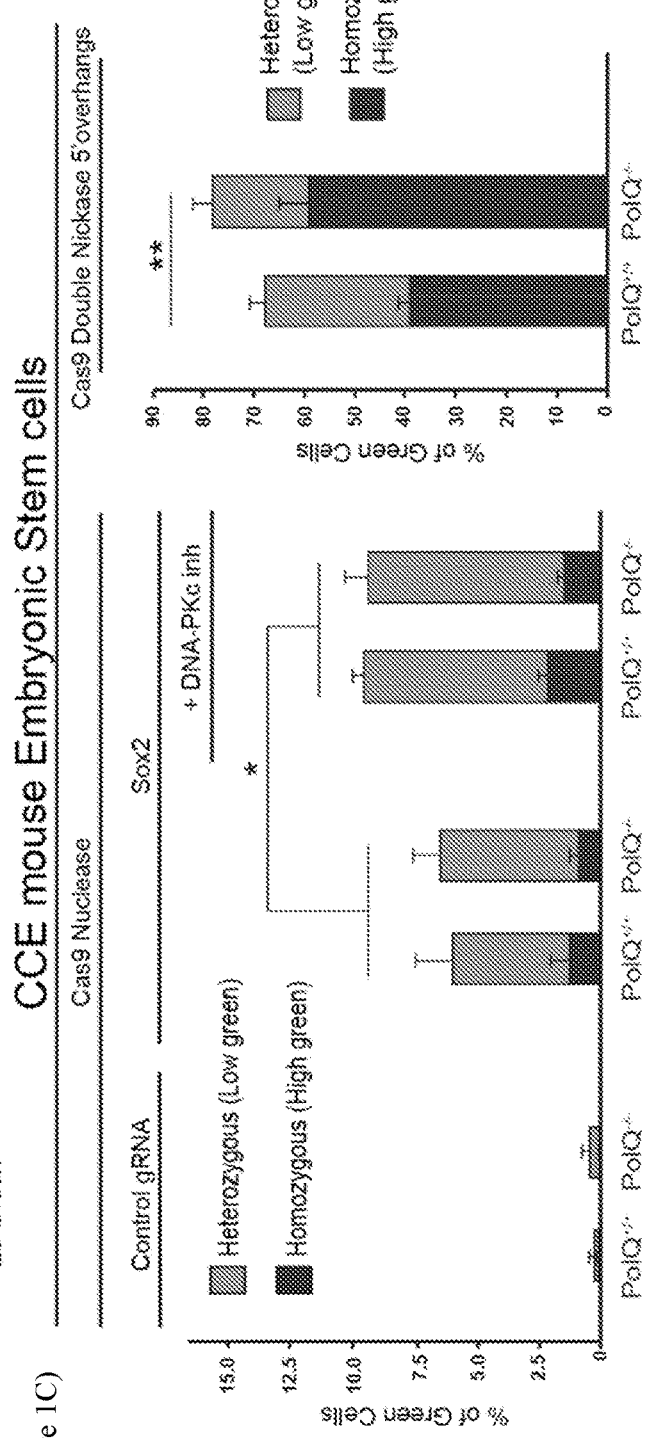
Figure 1D:
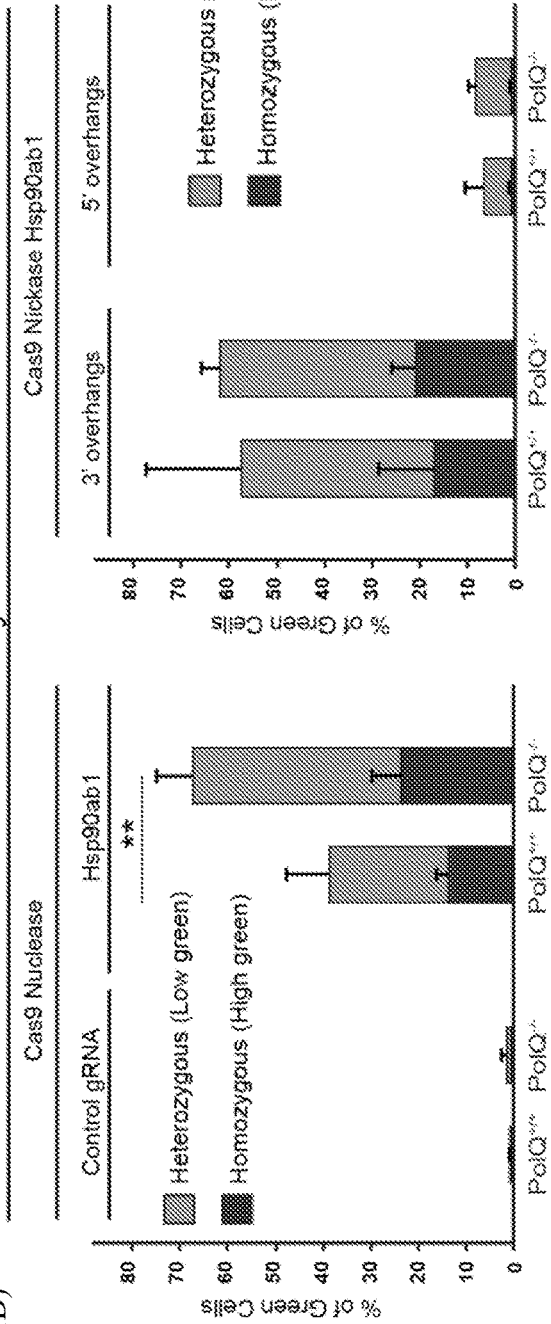
Figure 1E:
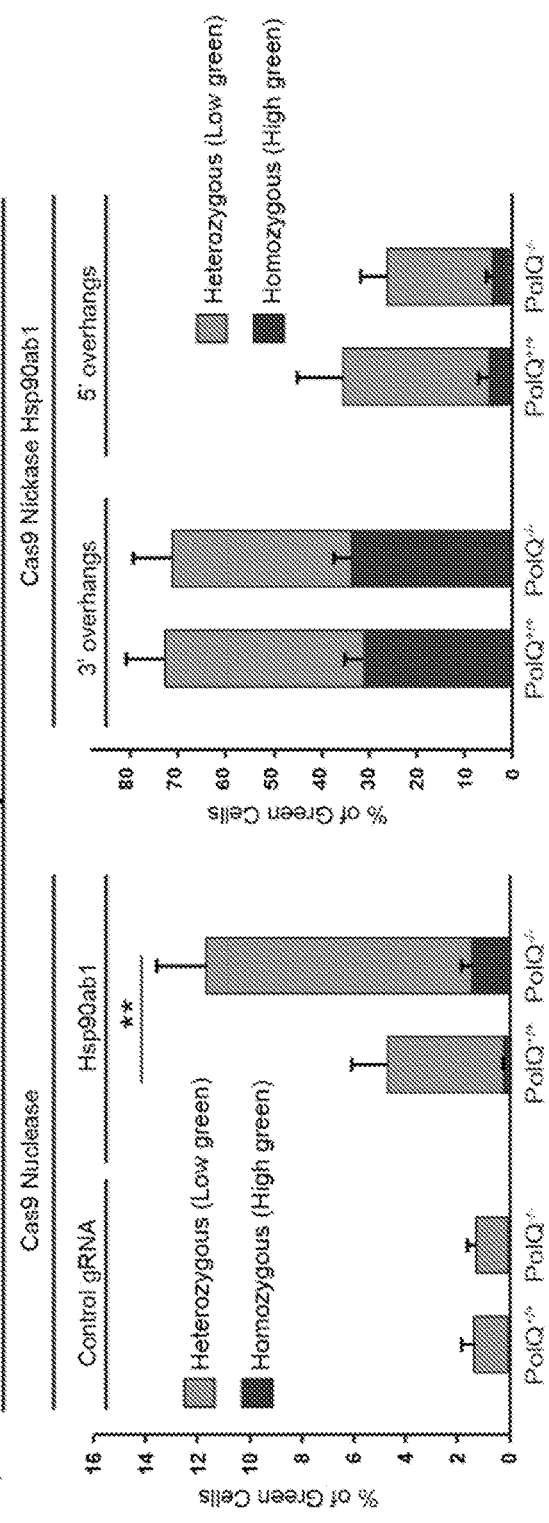

The present disclosure provides compositions and methods for enhancing CRISPR-mediated DNA editing facilitated by a Cas9 enzyme in mammalian cells. The disclosure is demonstrated using a non-limiting proof of principle as described further in Example 1 below which shows that it is possible to improve gene targeting efficiency in mammalian cells by combining Cas9 mediated targeting with POLQ inhibition. This is in contrast to results previously described using *C. elegans* as a model, where deletion of POLQ slightly decreased targeting efficiency of Cas9 nuclease (Van Schendel, Robin et al. "Polymerase Θ Is a Key Driver of Genome Evolution and of CRISPR/Cas9-Mediated Mutagenesis." Nature Communications 6 (2015): 7394. PMC. Jun. 16, 2015). Instead, as demonstrated in this disclosure, in mammalian cells the Cas9 targeting was enhanced by loss of the POLQ polymerase. Specifically, it was found: 1—that homozygous targeting (represented in FIG. 1C) is more enriched than heterozygous targeting when Cas9 nickase was used in CCE mESCs to insert ZsGreen at the end of sox2; 2—that homozygous and heterozygous targeting is more enriched in POLQ null mESCs and MEFs when Cas9 nuclease was used to introduce a cassette coding for ZsGreen at the 3'UTR of hsp90ab1. Thus, in various embodiments, the present disclosure comprises improving Cas9 mediated DNA editing in mammalian cells by concurrent inhibition of POLQ. In embodiments, the disclosure comprises use of Cas9 nickase and/or Cas9 nuclease. It will be recognized by those skilled in the art that the Cas9 nickase is a mutated version of a wild-type Cas9 nuclease. The nickase generates a single-stranded break (i.e., a nick) at a location based on a guide RNA as further described herein, while wild type Cas9 nuclease generates a blunt double stranded DNA break. In certain aspects, when the nickase is used with two gRNAs that introduce the nick close to one another in the DNA a double stranded break with overhangs can be generated. In embodiments, the CRISPR/Cas enzyme is the Cas9 enzyme having the amino acid sequence encoded by *Streptococcus pyogenes* Cas9.

In certain embodiments, improving Cas9 editing comprises increasing the number of chromosomes and/or the number of cells in which a chromosome is edited by the Cas9 relative to a control. In an embodiment, the control comprises an amount of Cas9 editing without concurrent suppression of POLQ. In an embodiment the control can comprise the amount of a DNA segment integrated into a chromosome using Cas9 editing as described herein without concurrent suppression of POLQ. In embodiments, the disclosure comprises using Cas9 nickase in CRISPR-mediated DNA editing in conjunction with POLQ suppression to increase homozygous editing relative to a suitable control. In embodiments, the disclosure comprises using Cas9 nuclease in CRISPR-mediated DNA editing in conjunction with POLQ suppression to increase both homozygous and heterozygous editing relative to a suitable control. In certain implementations comparisons of editing by Cas9 nickase to editing by Cas9 nuclease in conjunction with POLQ suppression can be made to determine differences in heterozygous and homozygous editing. The disclosure includes methods that pertain to populations of cells, whereby the percentage of cells in the population that comprise a homozygous or a heterozygous mutation is increased. Aspects of this and other embodiments of the disclosure can be related to any suitable reference, such as control value obtained directly or derived from editing performed without POLQ inhibition/suppression, i.e., editing performed in the presence of wild type amounts of POLQ.

In embodiments, methods of the disclosure comprise allowing expression of the Cas9 in the presence of a suitable gRNA such that a target DNA sequence is modified by Cas9 in a mammalian cell in which POLQ is inhibited. The targeted DNA can be any desired DNA sequence, provided it has the requisite sequence to be subject to cleavage by Cas9. In embodiments, targeting a particular DNA sequence is facilitated at least in part by selection of a suitable guide RNA (gRNA) sequence. Thus, as used herein Cas9 "targeting" means directing the Cas9 to a particular DNA sequence, i.e., a target locus, in a chromosome, and can thereby introduce an intended mutation that is present in a mutation template as further described below. The skilled artisan will appreciate a multitude of ways that are known in the art to design and introduce a suitable gRNA sequence into any mammalian cell or population of mammalian cells. Thus, in embodiments, a targeting RNA comprising a gRNA sequence is used. In general, the sequence of the targeting RNA has a segment that is the same as or complementarity to any CRISPR site in the target gene or other chromosomal region. In this regard, a suitable target sequence generally comprises a specific sequence on its 3' end referred to as a protospacer adjacent motif or "PAM". In an embodiment the target sequence conforms to the well-known N12-20NGG motif, wherein the NGG is the PAM sequence. Thus, in embodiments, the gRNA will comprise a segment that is from 12-20 nucleotides in length which is the same as or complementary to a DNA target sequence (a spacer) in the target DNA sequence. The 12-20 nucleotides directed to the spacer sequence will be present in the gRNA, regardless of whether the gRNA is comprised within, for example, a crRNA. In embodiments, a separate trans-activating crRNA (tracrRNA) can be used to assist in maturation of an RNA that is targeted to a particular gene. Introduction of a CRISPR system according to this disclosure into cells will result in binding of a targeting RNA/Cas9 complex to the target sequence so that the Cas9 can act on and cleave the target, and thus result in an alteration selected from a variety of modifications. In one embodiment, the cleaved sequence can be repaired by end joining DNA repair, which can result in either insertions or deletions at the break site, or by using a repair template to introduce mutations, or to introduce an inserted sequence. In embodiments, the disclosure includes administering an inhibitor of DNA-dependent protein kinase (DNA-PK) such that the classical NHEJ pathway of double DSB repair is inhibited. A number of DNA-PK inhibitors are known in the art and are commercially available; in a non-limiting example NU7441 is used.

In embodiments, a polynucleotide comprising or consisting of a gRNA can be introduced to a mammalian cell encoded by the same expression vector that also encodes the Cas9 enzyme, or it can be expressed from a distinct vector, or it can be introduced as RNA. The same applies for introducing polynucleotides encoding the Cas9. In more detail, any suitable expression vector can be used, and suitable expression vectors for introducing Cas9 encoding sequences, as well as gRNA sequences, as well as donor templates, are publicly available. In embodiments, the expression vector is a plasmid, or is a modified viral vector. In embodiments, the polynucleotide encoding the CRISPR system is transiently present in a cell. In embodiments, the polynucleotide encoding the CRISPR system is stably present in the cell, and/or may be integrated into a chromosome. Expression vectors can be introduced into cells using any suitable technique and delivery system, many of which are known in the art and include but are not limited to electroporation, lipid-based transfection systems, standard plasmid transformation approaches, such as by using competent cells, phage or viral transduction, micro-injection, including direct injection of a CRISPR vector or by introducing RNA itself. Additionally, expression systems/plasmids for use in CRISPR editing that include Cas9 nickase or Cas9 nuclease are publicly available from, for example, ADDGENE (Cambridge, Mass., USA).

In embodiments, an agent that inhibits POLQ, a Cas9 and a suitable gRNA targeting a desired DNA sequence are introduced into an individual for a prophylactic/and or therapeutic purpose. Thus, the disclosure includes pharmaceutical formulations comprising the CRISPR system reagents and/or POLQ inhibitors as described herein, and methods of administering them. In certain approaches a Cas9, a gRNA, a mutation template, and combinations thereof, can be introduced into cells which already have reduced or eliminated POLQ expression and/or function.

In certain approaches the disclosure comprises use of a donor template for use in modifying a chromosome at a target locus, and thus a donor template can also be considered a DNA mutation template. The DNA mutation template can comprise a DNA segment having any nucleotide length and homology with either DNA strand of the double-stranded chromosome segment comprising a target locus, so long as the length and sequence identity are adequate to introduce the intended mutation into the target locus via functioning of the CRISPR-Cas system described herein. In embodiments, the DNA mutation template is a single-stranded oligo DNA nucleotide (ssODN). In embodiments, the DNA mutation template is a double-stranded (ds) template. In embodiments, the DNA mutation template is provided as an episomal element, such as a plasmid or PCR product. In certain embodiments, the DNA mutation template is a ssODN having a length of from 20-2000 nucleotides (or base pairs if double-stranded), and in either case includes all integers from and including 20-2000, and all ranges there between. In embodiments, the homology of at least a segment of the DNA mutation template to the segment of the chromosome comprising the target locus comprises from 90%-100% identity with a contiguous segment of the chromosome, inclusive, and including all integers and ranges between 90%-100%. In embodiments, the mutation is flanked by homologous sequence segments with similarity above at least 80%. It will be recognized however, that the DNA mutation template can comprise regions that have less than 80%, or even no homology to the segment of the chromosome that comprises the target locus, and such regions can even be the majority of the template, so long as there is adequate homology between the DNA mutation template and the chromosome to participate in homologous recombination of a portion of the chromosome and the template that contains the mutation to be introduced. The degree of identity between homologous segments can be calculated exclusive of the mutation to be introduced. The DNA mutation template can comprise the intended mutation to be inserted into the chromosome.

The intended mutation can comprise or consist of a single nucleotide, or more than one nucleotide, and can be present in a protein-coding or non-protein coding portion of a chromosome, or may be present in a regulatory control element, including but not necessarily limited to a promoter or enhancer element, a splice junction, etc. The intended mutation may also be present in a DNA sequence that encodes for transcription of an RNA that is not an mRNA, such as a microRNA, tRNA, rRNA, etc. The intended mutation may introduce or remove a nucleotide that undergoes an epigenetic modification, such as a cytosine that is known to be methylated, or de-methylated during any of a variety of biological processes. Thus, the intended mutation can comprise or consist of a point mutation, an insertion, or a deletion, and will be dictated by the sequence of the mutation template and gRNA (so long as the other CRISPR-related elements, such as the NGG and PAM sequences are also present in appropriate proximity to the mutation site). In embodiments, the intended mutation comprises an insertion or deletion. In embodiments, the mutation comprises up to 20% of the nucleotides in the DNA mutation template. By introducing a mutation according to this disclosure, the characteristics of the resulting cells can be altered in a wide variety of ways, or the mutation can be silent, or its effects can be manifest conditioned upon the occurrence of a stimulus. In embodiments, the inserted mutation can convert the cell to a cell that is useful for modeling a disorder, and thus can be considered a pathogenic mutation. In embodiments, the mutation can comprise a selectable marker and/or a detectable marker.

The POLQ can be inhibited using any suitable approach, including but not limited to small molecule inhibitors, or by using polynucleotide targeting agents that will affect POLQ expression. Further, at least one anti-POLQ monoclonal antibody is commercially available, from, for example, SIGMA-ALDRICH. Thus, inhibiting POLQ comprises either inhibiting specifically or selectively inhibiting its enzymatic activity, or disrupting its expression, or a combination thereof. In embodiments, inhibiting POLQ comprises introducing into the cells a polynucleotide that can inhibit translation of POLQ mRNA, and/or can participate in and/or facilitate RNAi-mediated reduction of POLQ mRNA. The amino acid sequence of POLQ and its gene are known in the art. For example, the murine POLQ gene is publicly accessible under Gene ID: 77782 and the sequence of the human homologue is also known. In one embodiment, an antisense polynucleotide is used to inhibit translation of POLQ mRNA. Antisense nucleic acids can be DNA or RNA molecules that are complementary to at least a portion of the POLQ mRNA. In embodiments, oligomers of about fifteen nucleotides, and/or those that hybridize to the AUG initiation codon may be particularly efficient. The polynucleotides described herein for use in targeting POLQ mRNA can in certain embodiments be modified, such as to be resistant to nucleases.

In another aspect the disclosure includes RNAi-mediated reduction in POLQ mRNA. RNAi-based inhibition can be achieved using any suitable RNA polynucleotide that is targeted to POLQ mRNA. In embodiments, a single stranded or double stranded RNA, wherein at least one strand is complementary to the POLQ mRNA, can be introduced into the cell to promote RNAi-based degradation of POLQ mRNA. In another embodiment, microRNA (miRNA) targeted to the POLQ mRNA can be used. In another embodiment, a ribozyme that can specifically cleave POLQ mRNA can be used. In yet another embodiment, small interfering RNA (siRNA) can be used. siRNA (or ribozymes) can be introduced directly, for example, as a double stranded siRNA complex, or by using a modified expression vector, such as a lentiviral vector, to produce an shRNA. As is known in the art, shRNAs adopt a typical hairpin secondary structure that contains a paired sense and antisense portion, and a short loop sequence between the paired sense and antisense portions. shRNA is delivered to the cytoplasm where it is processed by DICER into siRNAs. siRNA is recognized by RNA-induced silencing complex (RISC), and once incorporated into RISC, siRNAs facilitate cleavage and degradation of targeted mRNA. In embodiments, an shRNA polynucleotide used to suppress POLQ expression can comprise or consist of between 45-100 nucleotides, inclusive, and including all integers between 45 and 100. The portion of the shRNA that is complementary to the POLQ mRNA can be from 21-29 nucleotides, inclusive, and including all integers between 21 and 29.

For delivering siRNA via shRNA, any suitable vector, including but not necessarily limited to lentiviral vectors, can be made and used according to standard techniques, given the benefit of the present disclosure. Further, suitable vectors expressing shRNAs targeted to many human mRNAs are commercially available. For example, several shRNA constructs provided in retroviral vectors are available from ORIGENE, (Rockville, Md., USA), and Applied Biological Materials (ABM) Inc., (Richmond, B.C., Canada), and can be included in methods and kits of this disclosure. Moreover, RNAi-mediated approaches for decreasing POLQ have already been demonstrated and can be adapted for use in embodiments of the present invention, given the benefit of this disclosure. In particular, as described in Mateos-Gomez et al., (*Mammalian polymerase θ promotes alternative NHEJ and suppresses recombination*, Nature, 2015 Feb. 12; 518(7538):254-7), from which the description of compositions and methods for inhibiting POLQ expression is incorporated herein by reference, delivery of shRNA targeted to POLQ mRNA efficiently reduces POLQ protein expression. Further, this is demonstrated in both mouse and human cells. Accordingly, in non-limiting embodiments, shRNA targeting POLQ sequences can comprise thesh Polq-1 (mouse sequence): 5'-CGGCGGAGTAT-GAGAACTATT-3' (SEQ ID NO:10); sh Polq-2 (mouse sequence): 5'-CCAGGAATCAAAGACGACAAT-3' (SEQ ID NO:11); sh Polq-3 (mouse sequence): 5'-CCTGGCT-GAATGCTGAACTTT-3' (SEQ ID NO:12); and sh POLQ (human sequence): 5'-CGGGCCTCTTTAGATATAAAT-3' (SEQ ID NO:13) that are demonstrated in Mateos-Gomez et al. It will be recognized that the shRNA itself comprises the RNA equivalent of the DNA sequences. It will also be recognized that minor variations in these sequences that do not reduce shRNA targeting of the mRNA can be made and are included within the scope of this disclosure.

Additionally, custom siRNAs or shRNA can be obtained from publicly available sources. Lentiviruses and other suitable retroviral constructs are capable of stably and permanently infecting target cells, such as by integrating into a chromosome.

In another aspect, the disclosure includes disrupting the POLQ gene such that POLQ mRNA and protein are not expressed. In one embodiment, the POLQ gene can be disrupted by targeted mutagenesis. In embodiments, the present disclosure provides for replacement of the POLQ gene with a sequence encoding a detectable marker, such as a fluorescent protein, or integrating such a sequence into the POLQ gene, thereby disrupting it, or integrating such a sequence elsewhere in the genome of the mammalian cells. By replacing POLQ or integrating a sequence encoding a detectable protein into it the disclosure provides for marking cells that do not express POLQ.

The disclosure includes inhibiting POLQ prior to introducing the Cas9 and gRNA sequence, or concurrently introducing a POLQ inhibitor to the cell with the Cas9-nickase and gRNA sequence.

As discussed above, the DNA that is selected to by modified using compositions and methods of this disclosure can be any suitable target DNA sequence. In embodiments, modification of the DNA confers a change in phenotype of the cell, such as a change in morphology, growth rate, expression of a detectable or selectable marker, or the modification is lethal to the cell. In embodiments, the DNA sequence that is modified is present on a chromosome, or is present on an extra-chromosomal element, including but not limited to a plasmid. In embodiments the modification can comprise insertion of a detectable marker into a DNA element in a cell. In embodiments, the disclosure includes modification of DNA in one or more cells, and can further comprise identification of one or more cells in which the modification occurs, or identification of cells wherein the modification does not occur, and separating such cells from one another to provide a population of isolated cells that, for example, contain a DNA modification made by the Cas9. In embodiments, the mammalian cells can be any mammalian cells, including but not limited to stem cells, such as totipotent, pluripotent, and multipotent cells. In embodiments the cells are hematopoietic cells. In embodiments, the cells are embryonic stem cells, or adult stem cells. In embodiments, the cells are epidermal stem cells or epithelial stem cells, or neuronal precursor cells. In embodiments, the cells are differentiated cells when the intended mutation is introduced. In embodiments, the cells are mammalian cells. In embodiments, the cells are human, or are non-human animal cells. In embodiments the disclosure includes progeny of any such cells, and non-human mammals comprising a cell or progeny of a cell made as described herein. In certain embodiments the cells modified according to this disclosure are not worm cells, including but not limited to cells of any nematode. In an embodiment, the cells modified according to this disclosure are not *C. elegans* cells.

In embodiments, the disclosure includes obtaining cells from an individual, modifying the cells ex vivo as described herein, and reintroducing the cells and/or their progeny into the individual for prophylaxis and/or therapy of a condition, disease or disorder, or to treat an injury, trauma or anatomical defect. In embodiments, the cells modified ex vivo as described herein are used autologously. In embodiments, the cells are provided as cell lines. In embodiments, the cells are engineered to produce a protein or other compound; the cells themselves or the protein or compound they produce in certain implementations may be useful for prophylactic or therapeutic applications.

In non-limiting examples, the mutation introduced into cells according to this disclosure is a homozygous dominant or homozygous recessive, or heterozygous dominant or heterozygous recessive mutation, that is correlated with a phenotype or condition, and is thus useful for modeling such phenotype or condition.

As described above, in embodiments, the disclosure includes identifying and separating cells that are heterozygous or are homozygous for a mutation introduced according to this disclosure. Such cells can be separated from one another, and from cells into which no mutation has been introduced. Identification and separation can be achieved using any suitable approach, including sequencing individual cells and expanding clones using routine approaches, or by including and detecting detectable markers, and/or other indicia of the mutation. In embodiments, the disclosure includes expanding separated cells to obtain a clonal population of the cells, and can further comprise promoting and/or allowing the cells to differentiate. Thus, the disclosure includes fully or partially differentiated cells that are homozygous or heterozygous for the introduced intended mutation. In embodiments, the disclosure includes compositions that include a cellular component, wherein the cellular component comprises or consists of cells modified according to this disclosure.

In an embodiment, the disclosure include a kit comprising a polynucleotides encoding a Cas9, and may further comprise an agent capable of inhibiting POLQ, or a polynucleotide that encodes a polynucleotide capable of disrupting POLQ expression. In non-limiting examples, the polynucleotide capable of disrupting POLQ expression is a commercially available viral vector that encodes an shRNA targeted to POLQ mRNA. The kit can further comprised a guide RNA or a polynucleotide encoding the guide RNA, or a vector adapted to insert and express a polynucleotide comprising a suitable gRNA segment. The kit can further comprised a polynucleotide or vector that is adaptable for expressing a mutation template.

EXAMPLE 1

The following specific Example is provided to illustrate the invention, but is not intended to be limiting in any way.

It will be apparent from this Example that a specific locus in cells with different genetic backgrounds was targeted, namely POLQ wild type and POLQ null backgrounds, using a ZsGreen reporter plasmid. Targeting was achieved with CRISPR/Cas9 editing tools, employing both the Cas9 nuclease and Cas9 nickase independently. To determine the efficiency of integration of the ZsGreen plasmid, the cells were subject to FACS sorting and the ZsGreen positive cells were quantified. In each case, a comparison of the % of ZsGreen+ cells in POLQ null to wild type cells was made. The results presented in FIG. 1, with particular amino acid and nucleotide sequences identified in FIGS. 2 and 4. The results presented in FIG. 1 show that POLQ inhibition had no impact on editing efficiency when using Cas9 nuclease to target sox2. In contrast, more efficient editing as evidenced by integration efficiency was achieved with Cas9 nickase with POLQ inhibition. Further, homozygous targeting (represented in FIG. 1) is more enriched than heterozygous targeting. In the case of hsp90ab1 locus targeting (FIG. 1), more homozygous and heterozygous editing was achieved with Cas9 nuclease in POLQ deficient mESCs and MEFs. Thus, this Example demonstrates the principle that improved Cas9 editing efficiency can be obtained by combining Cas9 with POLQ inhibition in mammalian cells. The improved efficiency of Cas9-Nuclease or Nickase targeting appears to be locus specific.

This Example provides: first, a demonstration of inserting into CCE mouse embryonic stem cells (CCE mESCs) a detectable marker (ZsGreen—a green fluorescent protein) at the end of the sox2 gene. A P2A sequence (57 nucleotides) followed by ZsGreen (696 nt) gene was inserted preceding the STOP codon of sox2. Second, a demonstration of inserting into mouse embryonic stem cells (mESCs) and mouse embryonic fibroblast (MEFs) a detectable marker (ZsGreen—a green fluorescent protein) at the end of the hsp90ab1 gene. A P2A sequence (57 nucleotides) followed by ZsGreen (696 nt) gene was inserted preceding the STOP codon of hsp90ab1. Therefore, in the case of correct targeting, the Sox2 or the Hsp90ab1 and ZsGreen proteins will be translated as distinct proteins from a single mRNA, transcription of which is controlled by the sox2 or hsp90ab1 promoters respectively. The experiments were performed in POLQ WT and POLQ null mouse cells.

Figure 4:
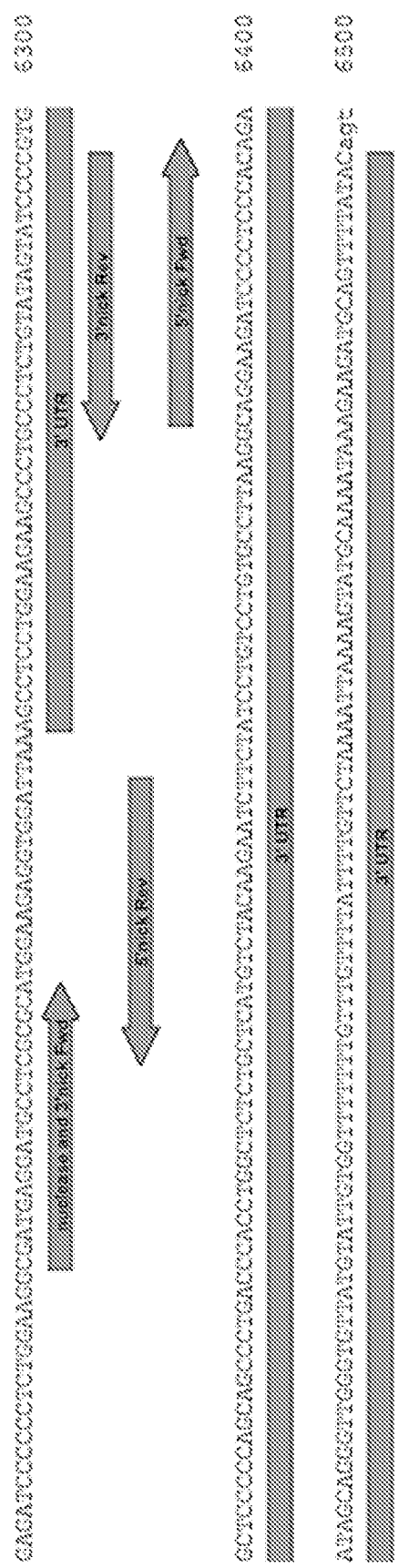
FIG. 4. Representative sequences used to illustrate embodiments of this disclosure. Boxes indicate segments of the sequences as labeled. The sequence contains the sequence that was subject to cleavage by Cas9-nuclease and by Cas9 nickase (D10A) in hsp90ab1. The Guide RNAs for Hsp90ab1 sequence is SEQ ID NO:6. The lower part (Template for Hsp90ab1) shows the sequence of the donor template used for the genome editing. The DNA sequence for the Template for Hsp90ab1 is SEQ ID NO:7.

To perform the experiment, the results of which are illustrated graphically in FIG. 1, and performed using the representative sequences shown in FIGS. 2 and 4, the following experimental approach and protocol was used. Those skilled in the art will recognize given the benefit of the present disclosure that alternative techniques and reagents could also be used.

Reagents

Two donor plasmids were generated as template for the targeting of Sox2 and Hsp90ab1 using pSL301 as a vector, to which the following three segments were introduced. 1—The last 831 nt or 700 nt of Sox2 or Hsp90ab1 genes without the STOP codon (used as a 5' homology arms in the donor plasmid), fused to 2—P2A-ZsGreen and followed by 3—the first 801 nt of the 3'UTR of Sox2 or the 700 nt after the STOP codon of Hsp90ab1 respectively (used as a 3' homology arm in the donor plasmid).

Cas9 nuclease and nickase D10A were expressed from publicly available expression vectors. In particular, pX330-U6-Chimeric_BB-CBh-hSpCas9 (Addgene plasmid #42230) and pX335-U6-Chimeric_BB-CBh-hSpCas9n (D10A) (Addgene Plasmid #42335), respectively. In both plasmids a Puromycin-cassette was inserted for selection, which serves to enrich for ES cells expressing the Cas9. With the Cas9 nuclease version one guide RNA (gRNA) was expressed (5'-CAGCCCTCACATGTGCGACA-3' (SEQ ID NO:14) for Sox2 and 5'-CGATGAGGATGCCTCGCGCA-3' (SEQ ID NO:15) for Hsp90ab1) and two gRNAs with the nickase version (5'-TTAATGGCCGTGCCGGGCAC-3' (SEQ ID NO:16; 5'-GTGAGGGCTGGACTGCGAAC-3' (SEQ ID NO:16) for the Sox2 that after cleavage generate ends with 5' overhangs; For the Hsp90ab1 targeting the couple 5'-CGATGAGGATGCCTCGCGCA-3' (SEQ ID NO:17) and 5'-GGGGATACTATACAGAGGGC-3' (SEQ ID NO:18) were used to generate ends with 3' overhangs, and the couple 5'-CCCTCTGTATAGTATCCCCG-3' (SEQ ID NO:19) and 5'-ATCCACCTCTTCCATGCGCG-3' (SEQ ID NO:20) were used to generate ends with 5' overhangs). The gRNAs were designed using crispr.mit.edu/ and cloned using www.genome-engineering.org/crispr/?page_id=23. In the case of the nickase both gRNAs were cloned in tandem U6 promoter-gRNA-1-U6 promoter-gRNA-2 using a KpnI restriction site located in the px335 plasmid downstream of the gRNA cloning site.

The mouse cells were CCE mES cells, mES cells and MEFs (all three WT and POLQ null). Lipofectamine® 3000 was obtained from Life Technologies. The culture media for CCE mESCs contained 500 ml of DMEM and 90 ml of ESC qualified FBS, supplemented according to manufacturer with non-essential amino acids, L-glutamine, penicillin/streptomycin, B-mercaptoethanol and LIF protein. The culture media for mESCs contained 500 ml of DMEM and 90 ml of ESC qualified FBS, supplemented according to manufacturer with non-essential amino acids, L-glutamine, penicillin/streptomycin, B-mercaptoethanol, LIF protein, PD03259010 (MEK inhibitor) 1 uM and CHIR99021 (GSK inhibitor) 3 uM. The culture media for MEFs contained 500 ml of DMEM and 50 ml of FBS, supplemented according to manufacturer with non-essential amino acids, L-glutamine, penicillin/streptomycin.

DNA-PK inhibitor was NU7441 (1 uM) was included to block classical-NHEJ.

The following protocol was used to obtain the results summarized in FIG. 1.

Transfecting plasmids into CCE mES cells:

Add 7.5 ul of Lipofectamine® 3000 to 50 ul of Opti-MEM® Reduced Serum Medium, incubate 5 min at RT.

Add 500 ng of Cas9 plasmid and 2000 ng of donor plasmid to 50 ul of Opti-MEM and then 5 ul of P3000 reagent.

Mix both solutions and incubate RT at least 5 min.

Detach the CCE mES cells and obtain a single cell suspension.

Count the cells and take 1 million. Spin down 4 min 300 g.

Aspirate the media and break up the cell pellet by manipulating the tube.

Add the solution (00030) to the cells, gently pipette up and down to make sure all cells are well resuspended. Incubate 10-12 min. Shake the tube to avoid cells precipitation.

After incubation, add 4 ml of medium and plate them in a 6 cm plate.

Place cells in the incubator overnight and change medium the following morning. Add puromycin to a final concentration of 2.5 ug/ml.

After 30 hours of selection with puromycin (approximately 48 hour after transfection) to enrich for Cas9 expressing cells, the medium was replaced with non-puromycin containing media and the selected cells were allowed to grow.

For cells treated with DNA-PK inhibitor, the inhibitor was added in parallel to puromycin selection.

For 8 days medium was changed on a daily basis and the cells were passaged as required.

Harvest the cells and prepare them for flow cytometry to quantify the percentage of cells stably expressing ZsGreen. FACS Signal is gated as low and high Zsgreen, which is likely to reflect one and two copies of the gene. Results are depicted in FIG. 1.

Transfecting plasmids into mES cells and MEFs:

Add 3 ul of Lipofectamine® 3000 to 50 ul of Opti-MEM® Reduced Serum Medium, incubate 5 min at RT.

Add 200 ng of Cas9 plasmid and 800 ng of donor plasmid to 50 ul of Opti-MEM and then 2 ul of P3000 reagent.

Mix both solutions and incubate RT at least 5 min.

Detach the mES cells or the MEFs and obtain a single cell suspension.

Count the cells and take 1 million. Spin down 4 min 300 g.

Aspirate the media and break up the cell pellet by manipulating the tube.

Add the solution (00044) to the cells, gently pipette up and down to make sure all cells are well resuspended. Incubate 10-12 min. Shake the tube to avoid cells precipitation.

After incubation, add 1 ml of medium and plate them in a well of a 12 well plate.

Place cells in the incubator overnight and change medium the following morning. Add puromycin to a final concentration of 0.5 ug/ml for mESCs and 2 ug/ml for MEFs.

For mESCs and MEFs respectively, after 48 or 72 hours of selection with puromycin to enrich for Cas9 expressing cells, the medium was replaced with non-puromycin containing media and the selected cells were allowed to grow.

For 8 days medium was changed on a daily basis and the cells were passaged as required.

Harvest the cells and prepare them for flow cytometry to quantify the percentage of cells stably expressing ZsGreen. FACS Signal is gated as low and high Zsgreen, which is likely to reflect one and two copies of the gene. Results are depicted in FIG. 1.

While the invention has been described through specific embodiments, routine modifications will be apparent to those skilled in the art and such modifications are intended to be within the scope of the present invention.

What is claimed is:

1. A method for increasing the number of cells that comprise a modification of a target DNA sequence in chromosomes in a population of mammalian cells, relative to a control value for modification of the target DNA sequence in a population of mammalian cells in which pol θ ("POLQ") is not inhibited, the method comprising introducing into the population of mammalian cells one or more polynucleotides encoding:
   i) a clustered regularly interspaced short palindromic repeats (CRISPR) associated Cas9 D10A nickase enzyme; and
   ii) two CRISPR guide RNAs (gRNAs) directed to the target DNA sequence in the cells so that the Cas9 D10A nickase introduces two single-stranded breaks in the targeted sequence;
   iii) introducing into the population of mammalian cells a DNA insertion mutation template, and
   iv) introducing into the population of mammalian cells an agent capable of inhibiting the POLQ, such that the DNA mutation insertion template is introduced into the target sequence in more cells in the population of mammalian cells, relative to the control value for modification of the target DNA sequence in a population of mammalian cells in which POLQ is not inhibited.

2. The method of claim 1 wherein the Cas9 and the gRNAs are encoded on a single expression plasmid.

3. The method of claim 1 wherein the Cas9 and the gRNAs are encoded on distinct expression plasmids.

4. The method of claim 1, wherein the population of mammalian cells comprises stem cells.

5. The method of claim 1, wherein the agent capable of inhibiting POLQ comprises a polynucleotide directed to a polynucleotide in the population of cells that encodes POLQ (POLQ targeting polynucleotide).

6. The method of claim 5, wherein the POLQ targeting polynucleotide is selected from the group consisting of an antisense oligonucleotide, an siRNA, an shRNA, a polynucleotide encoding an shRNA, a polynucleotide encoding a ribozyme, and combinations thereof.

7. The method of claim 1, wherein the insertion mutation template encodes a detectable marker.

8. The method of claim 1, wherein the cell is a non-human mammalian cell.

9. The method of claim 1, wherein the population of the mammalian cells that comprise the DNA mutation insertion template, and to which said agent is introduced, comprise more cells that comprise a homozygous insertion of the DNA mutation insertion template, relative to cells in said population that comprise a heterozygous insertion of the DNA mutation insertion template.

* * * * *